United States Patent [19]

Meybeck et al.

[11] Patent Number: 5,034,228

[45] Date of Patent: Jul. 23, 1991

[54] PHARMACEUTICAL COMPOSITION, IN PARTICULAR DERMATOLOGICAL OR COSMETIC, COMPRISING HYDROUS LIPIDIC LAMELLAR PHASES OR LIPOSOMES CONTAINING A RETINOID OR A STRUCTURAL ANALOGUE THEREOF SUCH AS A CAROTENOID

[75] Inventors: Alain Meybeck, Courbevoie; Philippe Michelon, Paris; Christiane Montastier, Maisons-Lafitte; Gárard Redziniak, Saint-Cyr-En-Val, all of France

[73] Assignee: Moet-Hennessy Recherche, France

[21] Appl. No.: 430,123

[22] Filed: Nov. 1, 1989

Related U.S. Application Data

[63] Continuation of Ser. No. 939,800, Dec. 9, 1986, abandoned.

[30] Foreign Application Priority Data

Dec. 11, 1985 [FR] France ............................ 85 18362

[51] Int. Cl.$^5$ .................. A61K 37/22; A61K 7/00
[52] U.S. Cl. .................. 424/401; 424/450; 436/829; 514/859
[58] Field of Search .............. 428/402.2; 424/450, 424/401; 436/829; 514/859, 863

[56] References Cited

FOREIGN PATENT DOCUMENTS

WO82/02833 9/1982 PCT Int'l Appl. .

OTHER PUBLICATIONS

Puisieux et al., "Les Liposomes Applications Therapeutiques", Technique et Documentation (Lavoisier), 1985.
Chemical Abstracts, vol. 88, No. 19, May 8, 1978, No. 132362W.
Carotenoid Organization in Membranes, Thermal Transition and Spectral Properties of Carotenoid-Containing Liposomes, Biochim, Biophysic, Acta (1978) 119-27.
Chemical Abstracts, vol. 101, No. 13, Sep. 24, 1984, No. 106051m.
Lipsomes Containing Various Carotenoids and Chlorophyll. Photobiochemistry and Photobiophysics, vol. 7 (1984) 205-219.

Primary Examiner—John S. Maples
Attorney, Agent, or Firm—Steinberg & Raskin

[57] ABSTRACT

This invention relates to a composition comprising hydrous lipidic lamellar phases or liposomes contaiing, as an active agent a retinoid or a structural analogue of retinoid, such as a carotenoid or tretinoin. These compositions are more efficient against acne and less irritant for the skin and they are used as a pharmaceutical composition, notably dermatological or cosmetic.

28 Claims, No Drawings

PHARMACEUTICAL COMPOSITION, IN PARTICULAR DERMATOLOGICAL OR COSMETIC, COMPRISING HYDROUS LIPIDIC LAMELLAR PHASES OR LIPOSOMES CONTAINING A RETINOID OR A STRUCTURAL ANALOGUE THEREOF SUCH AS A CAROTENOID

This is a continuation of application Ser. No. 939,800, filed 12/9/86, now abandoned.

BACKGROUND OF THE INVENTION

The present invention relates to pharmaceutical compositions, in particular dermatological or cosmetic, comprising hydrous lipidic lamellar phases or liposomes containing a retinoid or a structural analogue thereof such as a carotenoid.

It is well known that certain retinoids such as the tretinoin, are used in therapeutics, particularly in the treatment against acne.

Tretinoin or its homologues such as the 13-cis-retinoic acid or the etretinate are drugs which are commonly used at the present time for treating acne. The anti-acneic action of carotenoids is also known. Various galenic forms have been proposed among which the most active one is based on an alcoholic solution of tretinoin intended for local administration. In this connection, reference can be made to a medicine bearing the trade name of ABEREL ®. There are various formulations of ABEREL comprising 0.025%, 0.05% and 0.1% of tretinoin. The excipient is based on ethyl alcohol at 95°. The effects of tretinoin are summarized in the VIDAL dictionary, "Spécialités Pharmaceutiques Francaises", notably in the edition of 1985 and more complete comments can be obtained from the article of Lorraine Kligman et al published in "The Journal of Investigative Dermatology", Volume 73, no. 5, part I, pages 354–358, issued in 1979, with an experimentation on the skin of Hairless Rhino mice which is the most suitable model for experimenting in the inhibition of comedos. In this article, Kligman stresses that tretinoin has also a positive effect to remove folds and wrinkles from the skin of the Hairless Rhino mouse.

There are also medicines intended for oral administration containing retinoids such as the 13-cis-retinoic acid or the etretinate, for treating serious acnes, psoriasis and other serious keratinisation disorders.

The main drawback of the tretinoid is, by general path, its systemic toxicity (teratogenicity, and undesirable effects due to hypervitaminosis A), and by local path, its irritant action liable to require, in some cases, the stopping of the treatment. It is emphasized in the VIDAL dictionary, that this action characterized by a dry, slightly smarting erithema, located mainly around the mouth and on the neck, is directly connected to the activity of the product but, however, this action disappears when applications are spaced out.

According to some authors, the systemic toxicity of tretinoin, even by local path, is a factor limiting its use (see antepenultimate paragraph on page 357 of the aforesaid article).

Thus, it appears that the irritant effect of tretinoin is directly linked to its activity.

Moreover, it is stated that the ABEREL ® forms, as a conventional excipient, in a solution at 0.2% and 0.3%, which are strongly dosed with tretinoin, are contraindicated in acne and reserved for the treatment of keratinisation disorders.

Finally, the alcoholic solution used in the ABEREL ® forms, dosed at 0.025% also proves to show an irriting effect.

In a further therapeutic application, reference can be made to the Albert Kligman U.S. Pat. No. 3,856,934 relating to a composition for the depigmentation of the skin, containing tretinoin (also called acid A vitamin or also trans-retinoic acid).

Lorraine Kligman et al further report in the review "Connective Tissue Research", 1984, volume 12, pages 139–150 that tretinoin at a 0.05% dose when applied during 5 and 10 weeks, stimulates fibroblasts and favours the reparation of the damage caused by a ultraviolet irradiation. Thus, Kligman discloses in this article that tretinoin has an activity favouring the formation of a subepidermic reconstruction area, which is considered as favorable to "rejuvenate" the epidermis.

SUMMARY OF THE INVENTION

Thus, it is an object of the present invention to solve the new technical problem consisting in providing a new therapeutic formulation of active agents comprising retinoids, carotenoids or compounds with an analogous chemical structure, allowing to potentiate their efficiency while reducing their toxic effects, notably the irriting effect on the skin when some of them are locally applied.

The present invention allows for the first time to solve this new technical problem.

Thus, according to a first aspect, the present invention provides a pharmaceutical composition, in particular dermatological or cosmetic, comprising hydrous lipidic lamellar phases, characterized in that the said hydrous lipidic lamellar phases or the said liposomes contain, as an active agent, a retinoid or a structural analogue thereof such as a carotenoid, the said active agent being present in an efficient amount.

According to a particular embodiment, the retinoids are advantageously selected among tretinoin or its derivatives, in particular the salts or esters thereof; the 13-cis-retinoic acid or its derivatives, in particular the salts or esters thereof; the A vitamin or its esters such as acetate, propionate or palmitate; the etretinate. On the other hand, the aforesaid carotenoid is preferably selected among the group consisting in $\alpha$ or $\beta$-carotene, $\gamma$-carotene or $\delta$-carotene.

According to a preferred embodiment, the weight content of tretinoin with respect to the total composition is $10^{-6}$ to $10^{-3}$, preferably $5.10^{-6}$ to $10^{-4}$.

DESCRIPTION OF THE PREFERRED EMBODIMENTS

Naturally, the aforesaid hydrous lipidic lamellar phases or liposomes may also contain further hydrophobic substances such as sterols (sitosterol, cholesterol, stigmasterol, etc) as it is usual and has been described in French Pat. No. 2,521,565.

The aforesaid active agent can be combined with other therapeutically, dermatologically or cosmetically active agents. Thus, it is possible to combine this active agent with a complementary active or secondary agent incorporated either in the said lipidic layer of the liposome, and in this case its amount should not exceed 40% in weight of the whole lipidic phase, or in the water phase, according to their solubility. This complementary active agent can be chosen in particular among erythromycine, clindamycine, metronidazole or another antibiotic or antiseptic agent or the derivatives of the aforesaid agents. In this case, the content of this complementary active agent can reach 4% by weight for erythromycine, 2% by weight for clindamycine or 2% by weight for metronidazole with respect to the total composition. Thus, the usual concentrations of these complementary active agents can be used in combination with the aforesaid main active agent. A particularly efficient combination consists in a $5.10^{-5}$ concentration of tretinoin with 1% erythromycine.

It is also advantageous and in some very important cases to add the lipidic phase an antioxidizing agent in its normal proportions of use, such as the α-tocopherol, B.H.T. or TBHQ. Further, it is still advantageous to add the aqueous phase hydrosoluble antioxidizing agents such as ascorbic acid, sodium sulfite, sodium disulfite, EDTA and stabilizers such as citric acid, histidine in their normal porportions of use. Also, a compound constituting an ultraviolet filter can be provided. Preferably, the amount of the retinoid or its structural analogue such as carotenoid in the lipidic phase constituting the double layer of the lamellar phases or liposomes is not critical and may reach 40% by weight. Preferably, this amount is comprised between $10^{-4}\%$ and 10%, and still preferably between 0.01% and 5%.

The hydrated lipidic lamellar phases or liposomes according to the invention containing one or several of the aforesaid various components, can advantageously be submitted to a lyophilization, according to the usual techniques, so as to provide a lipidic powder. This powder may be kept a long time in the powder state without any alteration, and is dispersed in an appropriate aqueous medium for a further use, in order to prepare a pharmaceutical composition, in particular dermatological or cosmetic according to the invention.

This pharmaceutical, dermatological or cosmetic composition according to the invention can be formulated for a topic application in order to treat the various forms of acne, hyperkeratosis, psoriasis and other keratinisation disorders, to fight against the actinic cutaneous ageing due for instance to repeated exposures to the sun and against chronological cutaneous ageing, to lighten or remove pigmental skin spots, to favour cicatrization, to restore blood microvessels notably in the derm and to stimulate hair growth. This composition can also be prepared in a form suitable for oral administration, particularly for treating the various forms of acne, hyperkeratosis, psoriasis.

Further purposes, characteristics and advantages of the invention will appear in the light of the following explanatory description giving several examples only by way of illustration, hence not liable to restrict in any way the scope of the invention and reporting activity evaluation results of hyperacanthosis and irritation. The attached drawing shows the comedolytic activity according to the acid A vitamin concentration, either contained in liposomes (curve L-o-o-o) or in alcohol (curve A-ΔΔΔ). Percentages are given in weight unless otherwise specified.

EXAMPLE 1

Preparation of liposome suspensions containing tretinoin 2 g of soya lecithin and 0.1 g of tretinoin are dissolved in 30 ml dichloromethane in the presence of a lipophilic antioxidizing agent, e.g. 0.0006 g α-tocopherol.

The obtained solution can be treated to provide a suspension of liposomes through the well known evaporation process in a rotative container which consists in allowing the deposit of a lipidic layer in the rotary evaporator flask by evaporation of the solvent, and then the addition of water or a suitable aqueous solution.

The so-called reverse phase procedure described in French Pat. No. 2,399,242 can also be used. However, it is preferred to spray the obtained solution at 65° C., as described in French Pat. No. 2,521,565 so as to produce a fine powder which is dispersed in 200 ml of an aqueous solution buffered at a pH of approximately 7.5. Generally, a solution containing 0.8% NaCl and 1.5% $NaH_2PO_4$ called "phosphate buffer" is used together with an antioxydant stabilizer such as ascorbic acid with a 0.05% concentration.

Thus, after homogeneization either with ultrasounds, or in a homogenizer under pressure, e.g. according to the process described in French Patent No. 2,534,487, the said suspension of liposomes is obtained wherein the tretinoin concentration is about $5.10^{-4}$ and the lecithin concentration is 1%.

It will be noted that various dilutions can thus be carried out by changing the amount of tretinoin added at the beginning or by increasing the volume of the dispersion solution, which is an easy method to prepare various tretinoin concentrations.

EXAMPLE 2

Use of the compositions according to example 1 to make a pharmaceutical or cosmetic composition The use of the composition of example 1 as a pharmaceutical or cosmetic composition is checked by the following in vivo experimentations on the hairless Rhino mouse.

A —Comedolytic activity

In order to study the comedolytic activity on the hairless Rhino mouse, liposomes suspensions with 3% lecithin and variously dosed with tretinoin are used, respectively $10^{-6}$; $5.10^{-6}$; $10^{-5}$; $5.10^{-5}$; $10^{-4}$; $10^{-3}$; $3.10^{-3}$.

Solutions with a same tretinoin concentration are prepared in 95° alcohol containing 5% polyethylene glycol 400.

Further, control solutions are prepared, namely a first control solution containing only liposomes at 3% lecithin without tretinoin, a second composition containing only 95° alcohol with 5% polyethylene glycol 400.

Every such composition is applied daily for three weeks on the scapular area of the Hairless Rhino mice at a 0.1 ml dosis.

At the end of this period, the animals are sacrificed and biopsies are performed on the application area. An optical microscopy examination connected with an image analyzing computer allows to quantify the cuttings by measuring the comedo's diameter (D) and its aperture (d). This method for measuring the comedolytic activity is in accordance with the one described by Claude BONNE et al. in International Journal of Cosmetic Science 3,23-28 (1981).

Thus, for every animal, the average of ratio r=d/D allows to characterize the comedolytic activity of the composition. It is proceeded as usual with a composition according to the invention containing tretinoin in liposomes (composition L) by comparing with a control composition in which tretinoin is contained in an alcoholic solution (composition A). The control composition contains liposomes with 3% lecithin. The results obtained are plotted in curves A (composition A) and L (composition L) on the attached drawing and given on table 1 below.

In order to obtain the aforesaid relation $r=d/D$, the procedure has been changed with respect to the one described by Claude BONNE by counting all existing or potential comedos for a given length of the epidermis. Thus, all the d/D of every comedo is averaged by including the value $d/D=1$ for the open comedos which tend to disappear when observed.

No significant comedolytic activity is observed on control solutions.

TABLE I

| COMEDOLYTIC ACTIVITY | | |
|---|---|---|
| Concentration of Acid VITAMIN A (tretinoin) | in Liposome $r = d/D$ | in 95° alcohol + 55% PEG 400 $r = d/D$ |
| test | 0.58 | 0.64 |
| $10^{-6}$ | 0.64 | |
| $5.10^{-6}$ | 0.88 | |
| $10^{-5}$ | 0.95 | 0.67 |
| $5.10^{-5}$ | | 0.85 |
| $10^{-4}$ | 0.98 | 0.93 |

PEG = Polyethylene glycol.

From the curves on FIG. 1, it can be noted that the dose $10^{-5}$ of tretinoin contained in liposomes brings about a maximum comedolytic activity which is only reached at a $10^{-4}$ tretinoin dose in alcoholic solution. Hence the formulation of tretinoin in liposomes or hydrous lipidic lamellar phases is ten times more active.

It should be noted that the animal model (Hairless Rhino mouse) is substantially more sensitive than man, that is the maximum activity is reached at a lower concentration.

On the other hand, the efficiency threshold in the hairless Rhino mouse is at $5\times10^{-6}$ for tretinoin contained in the liposomes according to the invention whereas it is only $5\times10^{-5}$ for alcoholic solvent.

Thus, the invention allows to potentiate the activity of tretinoin by incorporating it into liposomes or more or less hydrous lamellar lipidic phases.

Let us now see the results as regards hyperacanthosis.

B—Hyperacanthosis

It is known that tretinoin raises the mitosis of the epidermis basement membrane cells which then rise to the horny layer and produce hyperacanthosis.

Hyperacanthosis (H) is determined on cuttings having been used to evaluate the comedolytic activity. The image analyzing computer measures the increase H of the epidermis thickness e of the animals treated with respect to the control animals, the control solution being the one based on liposomes at 3% lecithin.

The evaluation of hyperacanthosis is obtained from the following formula:

$$H = \frac{e^t - e^o}{e^o}$$

wherein $e_t$ is the epidermis thickness of the treated animals and $e_O$ the one of the control animals.

The results obtained are shown in table II below.

TABLE II

| Tretinoin concentration | Hyperacanthosis | | | | | |
|---|---|---|---|---|---|---|
| | LIPOSOMES | | | ALCOHOL | | |
| Thickening | 0 | $10^{-4}$ | $5\,10^{-4}$ | 0 | $10^{-3}$ | $3.10^{-3}$ |
| $H_1$(8 days) | 50.7 | 88.5 | 85.3 | 14.3 | 59.45 | 58.1 |
| $H_2$ (16 days) | 45 | 37.7 | 41.8 | 19.8 | 78.8 | 80.5 |
| $H = \frac{H_1 + H_2}{2}$ | 47.85 | 63.1 | 63.55 | 17.05 | 69.125 | 63.9 |

P.S.: Values obtained after 8 days and 15 days treatment have been listed, then averaged.

It is noted that tretinoin contained in liposomes provides much faster, in only eight days, an epidermis thickening, which is beneficial for the comedo's treatment whereas tretinoin in alcoholic solution only brings about such effect after some fifteen days.

On the other hand, it is also noted that in the case of liposomes, after 16 days, the epidermis thickening decreases, which is also favorable.

C. Irritation

Irritation is studied in the rabbit, which is a more suitable model than the Rhino mouse for this phenomenon.

The test products are applied daily at a 0.03 ml/cm² in open patch on the right hand flank of every rabbit in a group of six, the left-hand flank being a control. The treatment time is 2 weeks at the rate of 5 days a week. (i.e. 10 days' treatment).

One microscopic reading is carried out every day according to the protocol on irritation tests issued in the "Journal Officiel" published in February 1982. Erythema and oedema are marked from 0 to 4.

Irritation index I is the average sum of the marks erytheme +oedema per application day and per animal, according to the following formula:

$$I = \frac{\Sigma \text{erythema} + \Sigma \text{oedema}}{60}$$

When the irritation index I obtained is $\leq 0.5$, the treatment composition or product is considered as not irritant;

when I is included between 0.5 and 2, the product or composition is considered as slightly irritant;

when I is greater than 2 and $\leq 5$, the product or composition is considered as irritant;

when I is greater than 5, the product or composition is considered as very irritant.

The results obtained are shown in table III page 18. It is observed that the irritation phenomenon only appears when skipping to higher concentrations than in the comedolytic activity study. The concentrations tested were chosen depending on the results of the comydolytic activity, that is to say by proceeding at a concentration difference factor of 10 to carry out a comparison of irritation at an equal comedolytic activity, which is determining for the practitioner.

In such conditions, it is noted that both irritation values obtained for liposomes are markedly lower than the ones obtained for the alcoholic solution.

Of course, unlike the comedolytic activity study where the action-dose quantification is clear and accurate, the irritation evaluation is more fluctuating and only a global trend is obtained.

Therefore, it can be said that the incorporation of tretinoin into liposomes allows to obtain the same result in treating comedos with 10 times less product, without raising irritant effects, which may even tend to decrease.

Moreover, the possibility of treating cutaneous diseases such as acne with ten times lower tretinoin doses reduces accordingly the toxicity risk of the tretinoin which is often linked to the dose. In fact, quite a number of publications describe the toxicity of tretinoin and its structural homologues (C. E. Orfanos et al.; Hautarzt June 1981, 32 (6), pages 275-280; J. M. Wishart et al. New Zealand Med. J. Oct. 28, 1981, 94 (694) pages 307-308). Further to the irritation already mentioned, one may quote: hypervitaminosis A resulting notably in a generalized pruritus, loss of hair (C. E. Orfanos already referred to), bone tumors (exostosis) (P. E. Pochi, New England J. Med., Apr. 28, 1983, 308 (17) pages 1024-1025), dryness of mucous membranes, notably the lips (C. E. Orfanos already referred to), allergic dermatoses (C. Romaguera et al.; Contact dermatitis October 1980, 6 (6) P. 442) a teratogenicity evidenced in the animal (L. Newell-Morris et al., Teratology August 1980, 22 (1) p. 87-101; A. G. Hendrickx et al, teratology August 1980, 22 (1) pages 13-22; I. M. Taylor et al, teratology April 1980 21 (2) pages 193-7).

Thus, the results of the in vivo experimentations reported above allow to infer that the compositions according to the invention in which tretinoin is incorporated into liposomes or into hydrous lipidic lamellar phases can be used to prepare pharmaceutical or cosmetic compositions, particularly for the local treatment of acne at doses below the activity threshold in an alcoholic medium while practically inducing no irritation phenomenon.

In other words, the incorporation of tetrinoin into liposomes or hydrous lipidic lamellar phases has resulted in a particularly unexpected potentiation at very lowa doses of $5.10^{-6}$ to $10^{-4}$, without for that matter potentiating the irritation phenomenon, unlike what might be expected by a man of the art since the irritation was considered as directly linked to the activity. Thus, it is possible to reduce the dose for an equivalent comedolytic activity, by drastically reducing the irritation phenomenon risk.

EXAMPLE 3

Dermatological composition.

According to the preferred method of example 1, a suspension of liposomes is prepared containing:

| | |
|---|---|
| Tretinoin | 0.005 g |
| Hydrogenated soya lecithin | 5 g |
| Sitosterol | 0.5 g |
| α-tocopherol | 0.005 g |

Buffered aqueous solution containing antioxidants and preservatives, q.s. 50 g.

The said suspension is then mixed with 50 g of Carbopol gel 940 ® at 1.25%.

This final composition in gel form is specified in the treatment for acne in daily application on the skin area to be treated.

EXAMPLE 4

Dermo-cosmetic composition

The procedure is as in example 3, with the following composition:

| | |
|---|---|
| Tretinoin | 0.001 g |
| Hydrogenated soya lecithin | 1.0 g |
| Cholesterol | 1.0 g |
| α-tocopherol | 0.003 g |

The gel obtained is used for the cure of acneic skins.

EXAMPLE 5

Dermatologic composition

With the liposomes suspension of example 3 an equal amount of Carbopol 940 ® gel at 1.2k% containing preserving agents, antioxidants and a ultraviolet filter A+B is mixed at usual concentrations.

This gel can be used for treating solar elastosis.

EXAMPLE 6

Dermo-cosmetic composition

A liposomes suspension is made up according to example 1, containing:

| | |
|---|---|
| Tretinoin | 0.002 g |
| Hydrogenated soya lecithin | 10.00 g |
| Sitosterol | 1.4 g |
| α-Tocopherol | 0.06 g |
| "Phosphate Buffer" containing antioxidants and preserving agents q.s. | 100 g |

This suspension is mixed with 125 g Carbopol 940 ® gel at 1.25%.

The gel obtained is emulsioned with 50 g of an oily phase based on perhydrosqualene containing a ultraviolet A+B filter and a perfume.

The gelled emulsion obtained is used to regenerate the face and body skin, and as a dermic restructuration agent or a healing agent.

EXAMPLE 7

Lyophilized dermatological composition

A liposome suspension according to example 1 is made up as follows:

| | |
|---|---|
| Tretinoin | 0.005 g |
| Hydrogenated soya lecithin | 5 g |
| Sitosterol | 0.5 g |
| B.H.T. | 0.005 g |
| "Phosphate buffer", q.s. | 100 g | to which 5 g of glucose are added in the aqueous phase as a lyophilization adjuvent.

This suspension is lyophilized.

When about to use it, 1 g of the lyophilizat is mixed with 20 ml of sterile distilled water, in the presence of usual water-soluble preserving agents.

The extemporaneous suspension can be used for treating acne, hyperkeratosis or solar elastosis.

EXAMPLE 8

Lyophilized dermo-cosmetic composition

A lyophilizat is prepared according to example 7, using only 0.001 g tretinoin.

The suspension prepared at the time of application can be used for treating acneic skins, rough or wrinkled skins.

EXAMPLE 9

Dermatological composition

According to example 3, a gel is made up as follows:

| Tretinoin | 0.005 g |
|---|---|
| Soya lecithin | 5.0 g |
| Sitosterol | 0.5 g |
| Erythromycine | 1.0 g |
| α-tocopherol | 0.003 g |
| Excipients for gel, q.s. | 100 g. |

It will be noted that in the present case, erythromycine is introduced into the orgainc dichloromethane solution, before spraying.

The gel obtained is used for treating acne.

EXAMPLE 10

Dermotological composition

According to example 1, a lipidic spray powder is prepared, containing:

| Tretinoin | 0.005 g |
|---|---|
| Lecithin | 1.0 g |
| Sitosterol | 0.1 g |
| α-tocopherol | 0.003 g |

It is dispersed in a "phosphate buffer" containing 1% clindamycine chlorhydrate, together with antioxidants, q.s. 100 g.

A suspension of liposomes is obtained which contains clindamycine chlorhydrate in the encapsulated aqueous phase.

This suspension can be lyophilized. In this case, 100 ml of an aqueous glucose solution at 10% is added previously.

At the time of use, 1 g lyophilizate is mixed with 20 ml sterile distilled water together with the usual water-soluble preserving agents.

The extemporaneous suspension is advantageously used for treating acne.

EXAMPLE 11

Dermatological composition

A gel is prepared according to example 3. However the buffered aqueous solution contains hydroquinone.

The liposomes suspension before being mixed with the Carbopol 940® is as follows:

| Tretinoin | 0.005 g |
|---|---|
| Hydrogenated soya lecithin | 5.0 g |
| Sitosterol | 0.5 g |
| Liposoluble antioxidant | 0.2 g |
| Hydroquinone | 3.0 g |
| Sodium sulfite | 0.4 g |
| Ascorbic acid | 0.5 g |
| "Phosphate buffer" q.s. | 50 g |

The gel will be used in topical application for treating pigmental spots.

EXAMPLE 12

Dermo-cosmetic composition

Procedure is as in example 11 but the amount of tretinoin and hydroquinone is reduced.

The final gel composition is as follows:

| Tretinoin | 0.001 g |
|---|---|
| Hydrogenated soya lecithin | 5.0 g |
| Sitosterol | 0.5 g |
| Liposoluble antioxidant | 0.2 g |
| Hydroquinone | 2.0 g |
| Sodium sulfite | 0.4 g |
| Ascorbic acid | 0.5 g |
| Carbopol 940 ® gel at 1.25% q.s. | 100 g |

This gel is used for application on skin pigmental spots such as the so-called old age spots, to make them disappear or at least attenuate them.

EXAMPLE 13

Dermo-cosmetic composition

A liposomes suspension is prepared according to example 1 with the following composition:

| Tretinoin | 0.0005 g |
|---|---|
| Soya lecithin | 0.5 g |
| Cholesterol | 0.05 g |
| α-tocopherol | 0.0003 g |
| Aqueous excipients made up of a "phosphate buffer" of preserving agents, antioxidants and perfumed aqueous extracts, q.s. | 100 ml |

The suspension obtained is a lotion used to favour hair growth.

TABLE III

| RABBIT SKIN IRRITATION AFTER 15 DAYS' TREATMENT | | | | | | |
|---|---|---|---|---|---|---|
| | Irritation mean value | | | | | |
| Composition | | | | | | |
| Tretinoin concentration | Control (0) | $5.10^{-6}$ | $5.10^{-5}$ | $10^{-4}$ | $5.10^{-4}$ | $10^{-3}$ | $3.10^{-3}$ |
| in liposomes (invention) | 2.34 | NS | NS | 2.67 | 3.24 | | |
| in alcohol + PEG (comparative) 400 5% | 1.08 | NS | NS | | | 3.13 | 3.95 |

N.S.: not significative.

EXAMPLE 14

Dermatological composition

According to the preferred method of example 1, a powder A is prepared by atomization and has the following composition:

| Tretinoin | 0.05 g |
|---|---|
| Hydrogenated soya lecithin | 20.0 g |

-continued

| | |
|---|---|
| Erythromycine stearate | 10.0 g |
| Alpha-tocopherol | 0.05 g |

On the other hand, an aqueous solution B having the following composition is prepared:

| | |
|---|---|
| Ascorbyl acetate | 0.01 g |
| EDTA | 0.01 g |
| Saccharose | 5.0 g |
| Glycin | 2.5 g |
| Water q.s. | 100.0 g. |

1 g of powder A is then dispersed in 100 g of the solution B under magnetic stirring during 2 hours at room temperature.

A liposomes suspension is formed and this suspension is then homogeneized with ultrasounds at 4° C. during 10 minutes at a power of 200 W. The average size of the liposomes after homogeneization is 200 nanometers.

The obtained suspension of liposomes is lyophilized at −40° C. to give a powder which can be kept in a closed container during several years.

The lyophilized powder, with a view to use it for dermatological purposes, is stirred with an appropriate aqueous medium such as a gel of Carbopol 940® of low viscosity (about 100 to 1000 centipoises). The proportion of the lyophilized powder in the gel is for example 1%.

This gel is obtained extemporaneously and can be used for daily application on the skin so as to treat acne.

EXAMPLE 15

Dermo-cosmetic composition

A gel according to example 3 is prepared and has the following composition:

| | |
|---|---|
| A vitamin acetate | 0.2 g |
| Hydrogenated soya lecithin | 1.8 g |
| B.H.T | 0.02 g |
| Excipient for gel, q.s. | 100.0 g. |

In the present example, the A vitamin acetate and the BHT are introduced in the solution of dichloromethane before atomization.

When the obtained gel is applied on the skin, it favours the epiderm revival.

EXAMPLE 16

Dermo-cosmetic composition

A gel is prepared according to example 15, but the 0.2 g of A vitamin acetate are replaced by 0.4 g of A vitamin palmitate. The amount of lecithin is only 1.6 g.

This gel also favours the epidem revival.

EXAMPLE 17

Dermo-cosmetic composition

A gel is prepared according to example 3 and has the following composition:

| | |
|---|---|
| Beta-caroten | 0.2 g |
| Soya lecithin | 1.8 g |
| Alpha-tocopherol | 0.002 g |
| Excipient for gel, q.s. | 100.0 g. |

The obtained gel is emulsified with 100 g of an oily phase comprising perhydrosqualen containing some perfume.

The obtained gelled emulsion is used for preparing the skin before a sun exposure.

What is claimed is:

1. Composition for dermatological and cosmetic treatment, said composition comprising
   (i) a pharmaceutically acceptable carrier having dispersed therein
   (ii) hydrous lipidic lamellar phases or liposomes having an active ingredient incorporated within a lipidic phase constituting a bilayer of said lamellar phases or liposomes in an amount of less than 40% by weight of said lipidic phase,
   said active ingredient being
   (a) a retinoid other than tretinoin in a dermatological and cosmetically effective amount, or
   (b) tretinoin in an amount of $10^{-6}$ to $10^{-3}$ parts by weight of said composition,
   whereby application of said composition provides increased dermatological and cosmetic activity with reduced toxic effects.

2. Composition according to claim 1 and also including as additional active ingredient an antibiotic or antiseptic agent.

3. Composition according to claim 1, wherein said tretinoin.

4. Composition accordingly to claim 1 wherein said retinoid is selected from the group consisting of 13-cis-tretinoic acid, salts thereof, esters thereof, vitamin A, esters thereof and etritinate.

5. Composition according to claim 1 wherein (a) is selected from the group consisting of alpha-carotene, beta-carotene, gamma-carotene and delta-carotene.

6. Composition according to claim 1 wherein said active ingredient is distributed in a lipidic phase constituting a bilayer of said lamellar phases or liposomes in an amount of between about $10^{-4}$ and 10% by weight of said lipidic phase.

7. Composition according to claim 1 wherein said active ingredient is distributed in a lipidic phase constituting a bilayer of said lamellar phases or liposomes in an amount of between about 0.01-5% by weight of said lipidic phase.

8. Composition according to claim 1 and also including as additional active ingredient an antibiotic or antiseptic agent selected from the group consisting of erythromycin, clindamycin, metronidazole, and esters thereof.

9. Composition according to claim 1 and including clindamycin or an ester thereof in an amount of up to 2% by weight of the composition.

10. Composition accordingly to claim 1 and also including an ultraviolet filter.

11. Composition according to claim 1 in the form of a lyophilized lipidic powder.

12. Composition according to claim 1 wherein said active ingredient is tretinoin.

13. Composition according to claim 12 wherein said tretinoin is in an amount of $5.10^{-6}$ to $10^{-4}$ parts by weight.

14. Composition according to claim 1 and also including erythromycin or an ester thereof in an amount of up to 4% by weight of the composition.

15. Composition according to claim 14 wherein the amount of said erythromycin or ester thereof is about 1% by weight.

16. Composition according to claim 1 wherein the hydrous lipidic lamellar phases or liposomes contain a hydrophobic substance.

17. Composition according to claim 16 wherein said hydrophic substance is a sterol.

18. Composition according to claim 17 wherein said sterol is selected from the group consisting of sitosterol, cholesterol and stigmasterol.

19. Composition according to claim 1 and also including in the lipidic lamellar phases or liposomes an antioxidant and an aqueous phase containing a water soluble antioxidant.

20. Composition according to claim 19 wherein the antioxidant in the lipidic lamellar phases or liposomes is selected from the group consisting of alpha-tocopherol B.H.T. or T.B.H.Q. and said water soluble antioxidant is selected from the group consisting of ascorbic acid, sodium sulfite, sodium bisulfite and EDTA.

21. Composition according to claim 20 and also containing a stabilizer.

22. Composition according to claim 21 wherein said stabilizer is selected from the group consisting of citric acid and histidine.

23. Composition for the oral treatment of acne hyperkeratoisis and psoriasis, said composition comprising
   (i) a pharmaceutically acceptable carrier for oral administration having dispersed therein
   (ii) hydrous lipidic lamellar phases or liposomes having an active ingredient incorporated within a lipidic phase constituting a bilayer of said lamellar phases or liposomes in an amount of less than 40% by weight of said lipidic phase, said active ingredient being
      (a) a retinoid other than tretinoin in a dermatological and cosmetically effective amount, or
      (b) tretinoin in an amount of $10^{-6}$ to $10^{-3}$ parts by weight of said composition.

whereby administration said composition provides increased dermatological and cosmetic activity with reduced toxic effects.

24. Composition according to claim 23, wherein said tretinoin is in the form of a salt or ester thereof.

25. Composition for dermatological and cosmetic treatment, said composition comprising
   (i) a pharmaceutically acceptable carrier having dispersed therein
   (ii) hydrous lipidic lamellar phases or liposomes having an active ingredient incorporated within a lipidic phase constituting a bilayer of said lamellar phases or liposomes in an amount of less than 40% by weight of said lipidic phase, said active ingredient being
      a retinoid other than tretinoin in a dermatological and cosmetically effective amount,
   wherein application of said composition provides increased dermatological and cosmetic activity with reduced toxic effects.

26. Composition according to claim 25, wherein said retinoid is in the form of a salt or ester thereof.

27. Composition for dermatological and cosmetic treatment, said composition comprising
   (i) a pharmaceutically acceptable carrier having dispersed therein
   (ii) hydrous lipidic lamellar phases or liposomes having an active ingredient incorporated within a lipidic phase constituting a bilayer of said lamellar phases or liposomes in an amount of less than 40% by weight of said lipidic phase, said active ingredient being
      a tretinoin in an amount of $10^{-6}$ to $10^{-3}$ parts by weight of said composition
   wherein application of said composition provides increased dermatological and cosmetic activity with reduced toxic effects.

28. Composition according to claim 27, wherein said tretinoin is in the form of a salt or ester thereof.

* * * * *

UNITED STATES PATENT AND TRADEMARK OFFICE
CERTIFICATE OF CORRECTION

PATENT NO. : 5,034,228

DATED : July 23, 1991

INVENTOR(S) : Alain Meybeck, et al.

It is certified that error appears in the above—identified patent and that said Letters Patent is hereby corrected as shown below:

On title page, item

[75] Inventors: Alain Meybeck, Courbevoie; Philippe Michelon, Paris; Christiane Montastier, Maisons-Lafitte; Gérard Redziniak, Saint-Cyr-En-Val, all of France.

Signed and Sealed this

Ninth Day of March, 1993

Attest:

STEPHEN G. KUNIN

*Attesting Officer*  *Acting Commissioner of Patents and Trademarks*

UNITED STATES PATENT AND TRADEMARK OFFICE
CERTIFICATE OF CORRECTION

PATENT NO. : 5,034,228
DATED : July 23, 1991
INVENTOR(S) : Alain Meybeck, Philippe Michelon, Christiane Montastier and Gerard Redziniak It is certified that error appears in the above-indentified patent and that said Letters Patent is hereby corrected as shown below:

On title page, "28 Claims, No Drawings" should read --28 Claims, 1 Drawing Sheet--

The drawing sheet, consisting of Fig. 1, should be added as shown on the attached page.

Signed and Sealed this

Seventh Day of June, 1994

Attest:

BRUCE LEHMAN

Attesting Officer

Commissioner of Patents and Trademarks

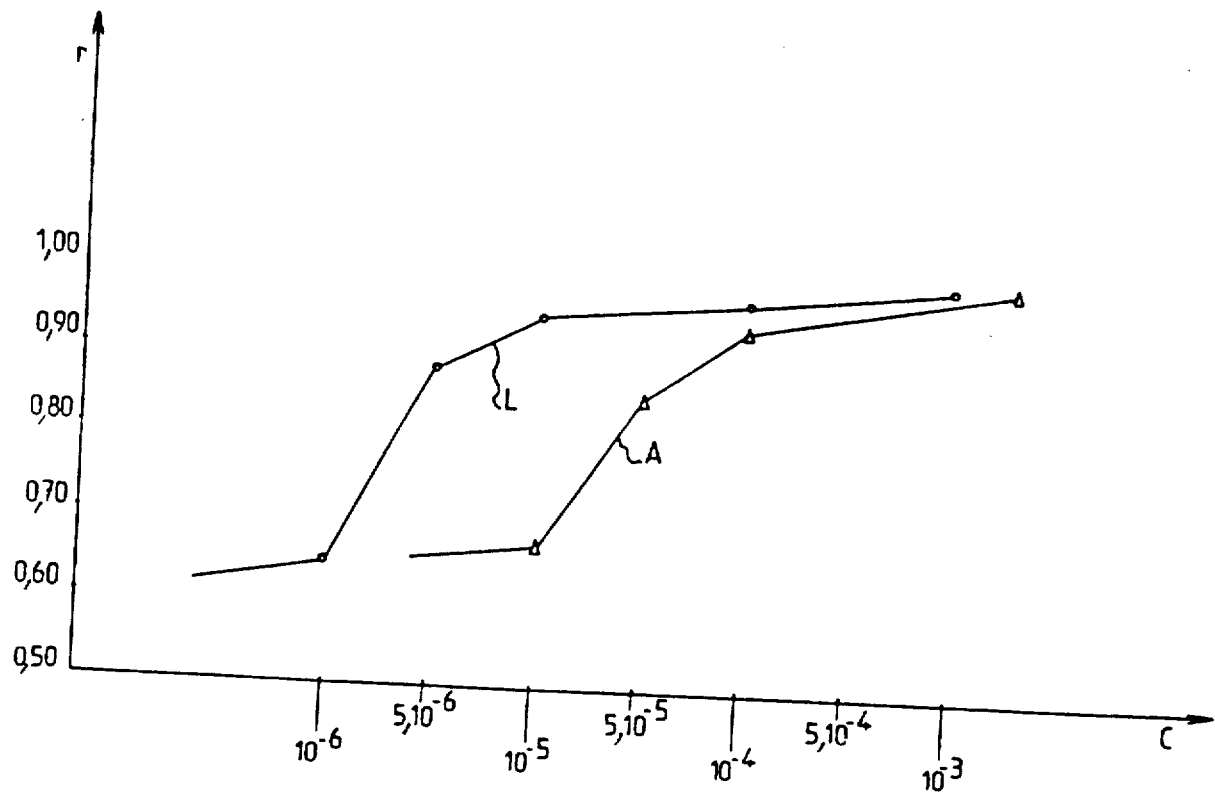

UNITED STATES PATENT AND TRADEMARK OFFICE
CERTIFICATE OF CORRECTION

PATENT NO. : 5,034,228
DATED : July 23, 1991
INVENTOR(S) : Alain Meybeck, Courbevoie; et al.

It is certified that error appears in the above-indentified patent and that said Letters Patent is hereby corrected as shown below:

On title page, item

[75] Inventors: Alain Meybeck, Courbevoie; Philippe Michelon, Paris; Christiane Montastier, Maisons-Lafitte; Gérard Redziniak, Saint-Cyr-En-Val, all of France.

The claim should be amended to read as follows:
Col. 12,

3. Composition according to claim 1, wherein, said <u>active ingredient is</u> tretinoin.

Signed and Sealed this

Tenth Day of January, 1995

Attest:

BRUCE LEHMAN

*Attesting Officer*   *Commissioner of Patents and Trademarks*